US006949223B2

(12) United States Patent
McEllen

(10) Patent No.: US 6,949,223 B2
(45) Date of Patent: Sep. 27, 2005

(54) LIGHT MODULE FOR AIR TREATMENT UNITS

(75) Inventor: John J. McEllen, Chagrin Falls, OH (US)

(73) Assignee: Guardian Technologies LLC, Beachwood, OH (US)

( * ) Notice: Subject to any disclaimer, the term of this patent is extended or adjusted under 35 U.S.C. 154(b) by 0 days.

(21) Appl. No.: 10/673,806

(22) Filed: Sep. 29, 2003

(65) Prior Publication Data

US 2005/0069465 A1 Mar. 31, 2005

(51) Int. Cl.[7] .............................................. A62B 11/00
(52) U.S. Cl. ...................... 422/120; 422/24; 422/121; 250/435; 250/436; 362/217
(58) Field of Search .............. 250/492.1, 435, 250/436; 422/120, 24, 121; 362/217, 226

(56) References Cited

U.S. PATENT DOCUMENTS 6,589,486 B1 * 7/2003 Spanton ...................... 422/121
6,797,966 B2 * 9/2004 Summers et al. ......... 250/492.1
6,838,057 B2 * 1/2005 Russell et al. ............... 422/121
2003/0039577 A1 * 2/2003 Nelson et al. .................. 422/4

* cited by examiner

Primary Examiner—John Kim
Assistant Examiner—Brad Chin
(74) Attorney, Agent, or Firm—Renner, Kenner, Greive, Bobak, Taylor & Weber

(57) ABSTRACT

The present invention provides an air treatment unit including a module power socket; an air treatment duct having an interior defining an air path; and an ultraviolet light module that selectively engages the air treatment duct, the ultraviolet light module including a housing having a baffle; an integral ultraviolet light source and light source socket, the ultraviolet light source being fixed to and extending through the baffle; and a connector that selectively mates with the module power socket, the connector being in power transmissive communication with the light source socket, wherein, when the ultraviolet light module selectively engages the air treatment duct and the connector selectively mates with the module power socket, the ultraviolet light module cannot be fully removed from its engagement with the air treatment duct without disconnecting the power.

3 Claims, 5 Drawing Sheets

LIGHT MODULE FOR AIR TREATMENT UNITS

TECHNICAL FIELD

The present invention generally relates to air treatment systems employing ultraviolet (UV) energy, particularly UV-C energy in the range of about 100 to about 280 nanometers, to disable various airborne microorganisms, including bacteria cells, virus cells, and mold spores. More particularly, this invention relates to an ultraviolet light module for use in air treatment systems, wherein the module provides safety features for preventing harmful exposure to UV energy.

BACKGROUND OF THE INVENTION

UV-C energy sources have been used by hospitals, microbiology labs, and food and water and other industries to disable microorganisms that are airborne and/or on work surfaces and equipment and the like. Generally, UV energy sources have been incorporated into irradiation systems and air circulation and ventilation systems to expose harmful microorganisms to UV-C energy in order to reduce the potential for exposure to such microorganisms.

A primary limitation on the use of UV-C energy sources for ultra violet germicidal irradiation (UVGI) is the difficulty in safely operating and maintaining systems employing the technology. Short-wave, high-energy UV-C radiation, which has a wavelength from about 100 to 280 nanometers, can cause mild to severe reddening of the skin and painful injury to the eye.

A copending patent application, Ser. No. 10/389,822, entitled "Air Treatment System for Localized and Personal Use," employs UV light in a sterilization unit particularly designed for, although not limited to, individual use, and it is envisioned that the device therein would benefit from being safely serviceable by the end consumer. Particularly, it is appreciated that the UV bulb that is the source of UV light for the sterilization unit has a limited life span, and, upon burning out, must be replaced with a new UV bulb. It would be desirable to allow for replacement of the UV light source by the end consumer of the sterilization unit. However, because exposure to UV light is harmful, especially direct exposure to the eyes, there is a need to design replacement UV light sources with safety features that prevent such direct exposure to UV light.

SUMMARY OF THE INVENTION

In general, the present invention provides an air treatment unit comprising: a module power socket; an air treatment duct having an interior defining an air path; and an ultraviolet light module that selectively engages the air treatment duct, the ultraviolet light module comprising: a housing having a baffle, the baffle extending across the air path when the ultraviolet light module engages the air treatment duct; an integral ultraviolet light source and light source socket, the ultraviolet light source being fixed to and extending through the baffle, such that the interior of the air treatment duct is exposed to ultraviolet light from the ultraviolet light source when the ultraviolet light module engages the air treatment duct and the ultraviolet light source is powered; and a connector that selectively mates with the module power socket, the connector being in power transmissive communication with the light source socket, wherein, when the ultraviolet light module selectively engages the air treatment duct and the connector selectively mates with the module power socket, the ultraviolet light module cannot be fully removed from its engagement with the air treatment duct.

In a preferred embodiment, the ultraviolet light module is intended to be a replaceable unit in an air treatment device that employs ultraviolet light. Because exposure to UV light should be avoided, the ultraviolet light module allows for safe replacement of spent ultraviolet light sources (e.g., UV light bulbs). Rather than having to access and manipulate the light source directly to replace it when it is spent or otherwise faulty, the entire module can be removed. Due to its design, when removing a module for any reason, the power to the UV light source is disconnected before the module is removed, such that the person servicing the air treatment device is not likely to directly expose himself to a powered UV light source. Similarly, when replacing one module with another, the module is fitted to the air treatment duct before the power to the UV light source is engaged (at the connector and module power socket), and the person replacing the module is not likely to directly expose himself to a powered UV light source. In one embodiment, a power switch is located in the top cap of the air treatment device and when the power switch is adjusted to an "off" position, no power flows to the UV light source. This provides an additional safeguard to ensure that the person servicing the air treatment device is not likely to directly expose himself to a powered UV light source.

When the light module is in place in the air treatment device, the baffle extends across the air path when the UV light source is powered up. The baffle maintains the correct rate of airflow and also blocks much of the UV-C energy that may otherwise be transmitted if the cap is removed without unplugging or turning off the air treatment device during maintenance or cleaning of the device. The light module of the present invention must be removed from the device in order to clean the device and replace the light source, and when the light module is removed, the power to the light source is perforce disconnected.

These and other benefits will be appreciated with reference to the detailed description below. And those of ordinary skill in the art will readily appreciate the application of the present light module concept in air treatment devices other than the particular device depicted herein.

BRIEF DESCRIPTION OF THE DRAWINGS

For a complete understanding of the objects, techniques and structure of the invention, reference should be made to the following detailed description and accompanying drawings wherein.

DETAILED DESCRIPTION

Figure 1:
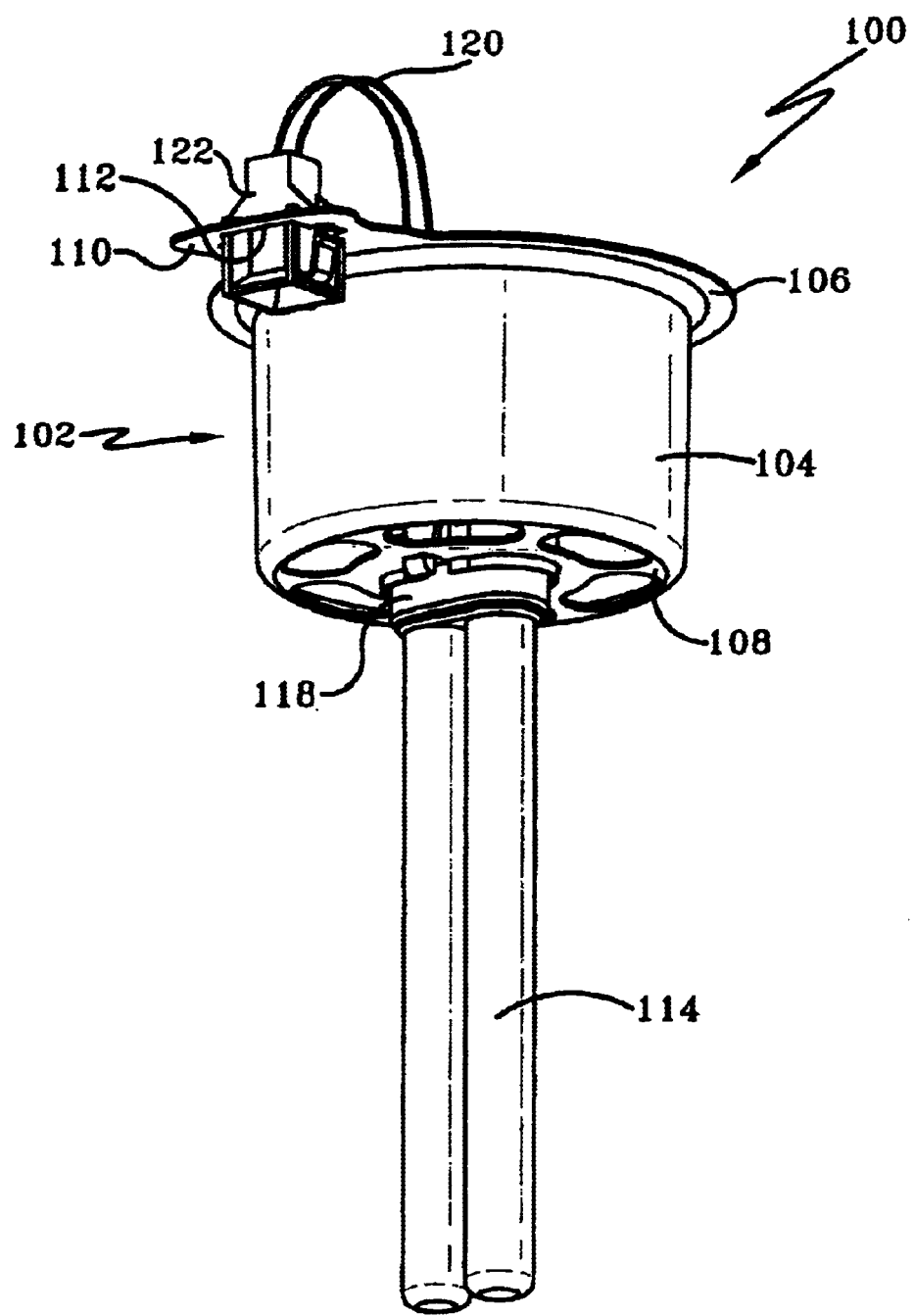
FIG. 1 is a perspective view of a light module according to this invention.
Figure 2:
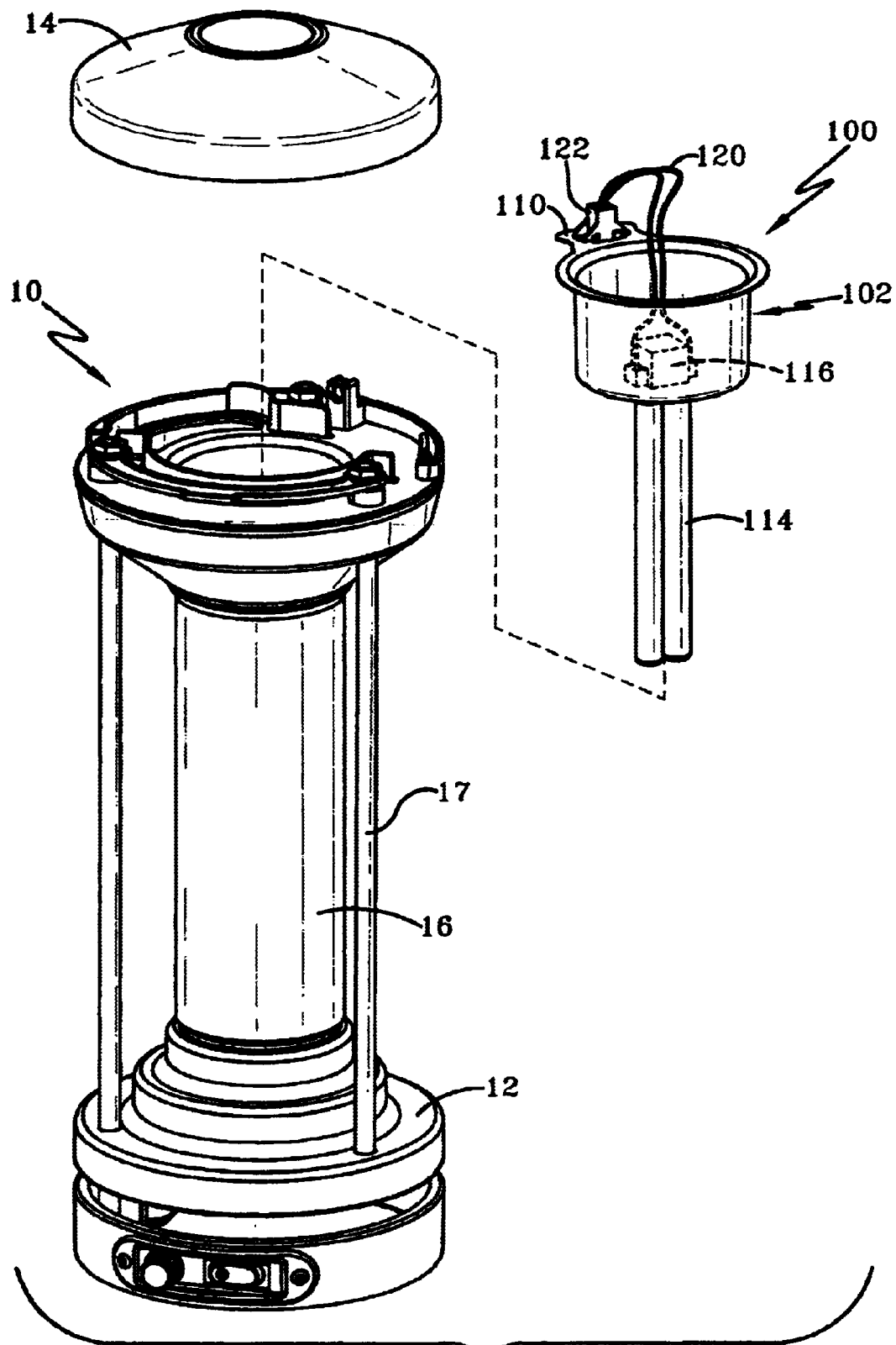
FIG. 2 is an assembly diagram of a light module according to this invention, portions thereof being shown in phantom when hidden from direct view in the perspective shown.

Referring now to FIG. 1, a light module according to this invention is shown and designated generally by the numeral 100. Light module 100 includes a housing 102 defined by a sidewall 104 extending between a lip 106 and baffle 108. A connector flange 110 with an aperture 112 is formed as part of housing 102, and preferably is formed in lip 106, as shown.

Figure 3:
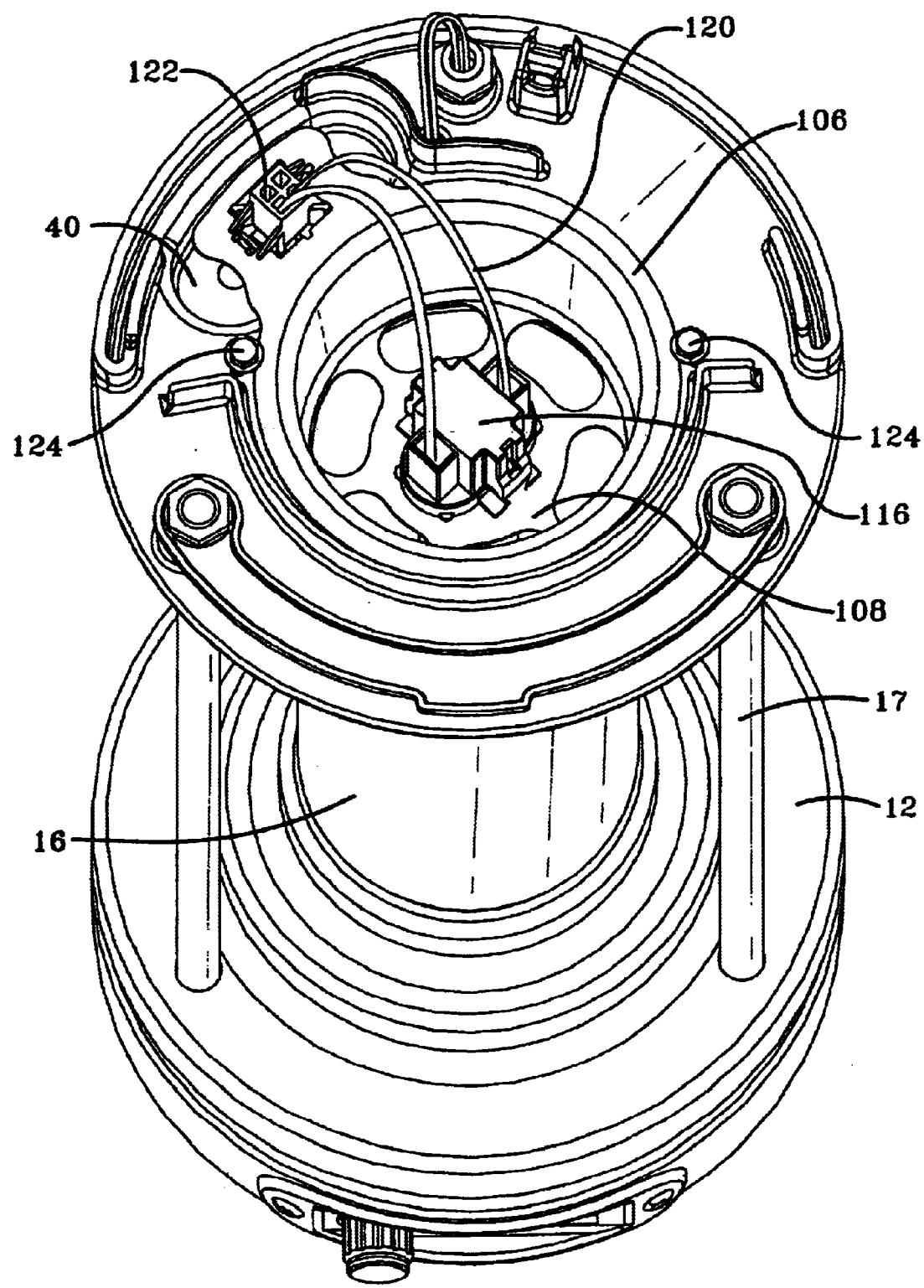
FIG. 3 is a perspective view of a light module according to this invention, seated within an air treatment unit.
Figure 4:
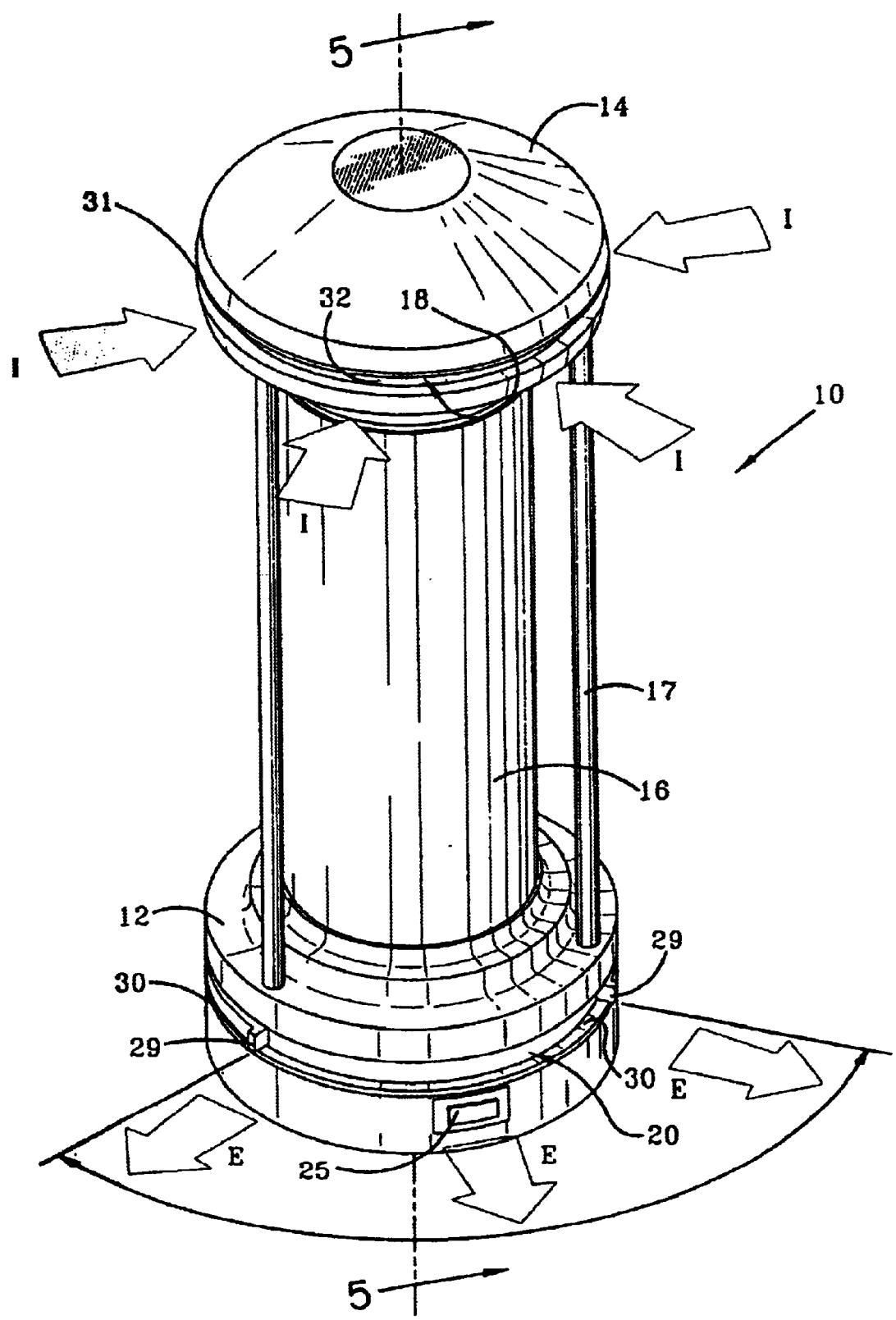
FIG. 4 is a front plan view of a particular air treatment unit that receives a light module according to this invention.

A UV light source 114 is fixed to baffle 108. As used herein, "fixed" is not necessarily to be understood as defining that UV light source 114 is directly fixed to baffle 108. Rather, in preferred embodiments, such as that shown, UV light source 114 is bonded to light source socket 116 (shown in FIG. 3) to be integral therewith, light source socket 116 is bonded to one side of baffle 108, and UV light source 114 extends through an aperture 118 in baffle 108 to extend on the other side thereof. Although not directly fixed to baffle 108, UV light source is considered "fixed" thereto inasmuch as its position is substantially dictated by the positioning of baffle 108 and housing 102.

Wires 120 extend from light source socket 116 to connector 122. Wires 120 are sufficiently long that connector 122 may align with aperture 112, and, in a particularly preferred embodiment, connector 122 is bonded to connector flange 110 substantially as shown. This structure defines an entire light module 100 that will have application in air treatment units having certain structural elements. A particular embodiment of an air treatment unit into which light module 100 is advantageously incorporated is referred to below in order to help demonstrate the benefits offered by the light module concept of this invention. The means for incorporating this concept into air treatment units somewhat dissimilar to the preferred air treatment unit below will be readily appreciated.

Light module 100, in the preferred embodiment shown, is designed to be incorporated into an air treatment unit 10 shown in FIGS. 2–5. This air treatment unit 10 is substantially identical to the air treatment unit disclosed in copending U.S. patent application Ser. No. 10/389,822, but differs in that light module 100 is incorporated into the design. The entirety of the copending application is incorporated herein.

Unit 10 is generally cylindrical, as shown, and includes a base portion 12 and top portion 14, with an air treatment duct 16 communicating therebetween. Each of these elements, and, thus, the general shape of unit 10 need not be cylindrical, as shown, and, indeed, any general shape of unit 10 may be employed and yet fall within the scope of the present invention.

Tubing 17, which is generally employed for both aesthetics and, in particular embodiments, for providing a wire way for a power supply, as will be described below, communicates between base portion 12 and top portion 14. Tubing 17 may be hollow for provision of a wire way.

Figure 5:
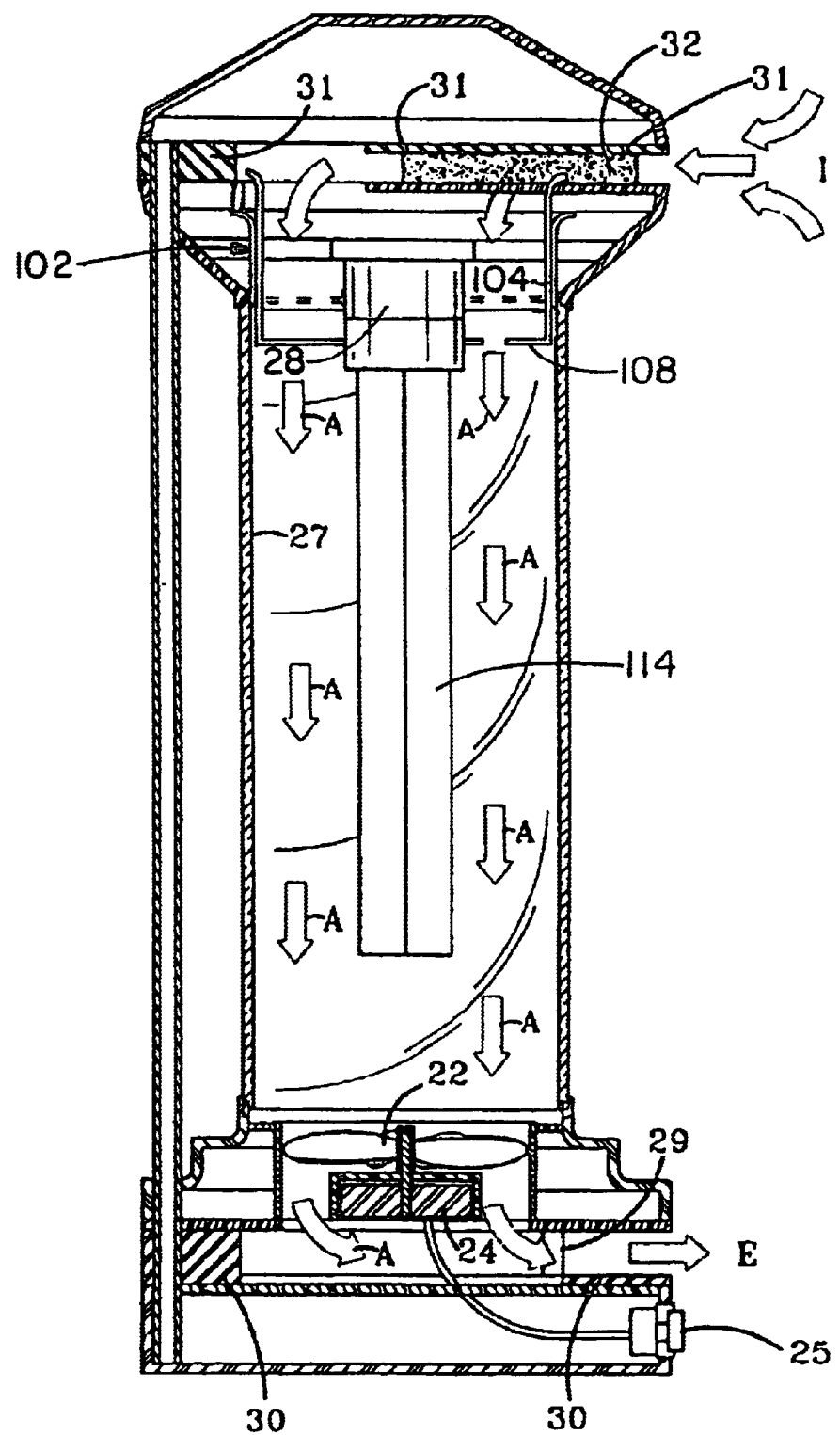
FIG. 5 is a cross-sectional view of the air treatment unit of FIG. 4, taken along the line 2—2.

An intake port 18 is provided in top portion 14 and an exhaust port 20 is provided in base portion 12, and each of these ports 18, 20 communicates with the interior of air treatment duct 16 to create an air path, during operation of unit 10, that is generally represented by the arrows designated by the letter A, in the cross-sectional view of FIG. 5. In operation, intake air (represented by arrows I) is directed along air path A by means of fan 22, which is located in base portion 12. Fan 22 is operated by a conventional motor 24, which connects to a suitable power source through conventional methods, and is operable by connection (represented by a non-numbered wire in FIG. 2) to a conventional on/off switch 25. For instance, as suggested in FIG. 2, an electric cord may connect to motor 24 and run externally of base 12 to be plugged into a suitable power outlet, or alternatively, motor 24 could be battery operated, and a conventional on/off switch 25 could connect or disconnect the flow of power to motor 24, through known methods.

Although other measures might be taken, in one embodiment UV-absorbing adjustable spacer 30 and UV-absorbing spacer 31 are respectively provided in bottom portion 12 and top portion 14. Particularly, spacers 30, 31 help define exhaust port 20 and intake port 18.

When activated, fan 22 draws intake air I at intake port 18 and draws the air downward, through air treatment duct 16, as represented by air path A, and out exhaust port 20, as exhaust air E. Along air path A, air may be filtered by a primary filter 32 and, thereafter, continue into sterilization duct 16.

Light module 100 selectively engages air treatment unit 10. More particularly, lip 106 rests on the top edge of air treatment duct 16 and extends along the lower surface of intake port 18. Insofar as spacers 31 are present and help define intake port 18, lip 106 may rest on a surface of spacer 31. Sidewall 104, baffle 108 and light source 114 extend from lip 106 into air treatment duct 16. Light module 100 may be further held in place by means of one or more retaining screws 124.

Additionally, light module 100 selectively engages air treatment unit 10 where connector 122 mates with module power socket 40. In a preferred embodiment, light module 100 includes connector flange 110 and connector flange 110 includes an aperture 112 that aligns with module power socket 40 when light module 100 selectively engages air treatment duct 16. Preferably, connector 122 extends through aperture 112 and selectively mates with module power socket 40.

Light module 100 engages air sterilization duct 16 such that baffle 108 extends across at least a portion of the air path defined within air treatment duct 16, with UV light source 114 residing in the interior of air treatment duct 16. Preferably, baffle 108 is shaped to fit across the entire cross section of the air path. As its name implies, baffle 108 serves to help regulate air flow through air treatment duct 16, and includes a plurality of apertures 124 for this purpose. The shape and number of apertures 124 maybe selected to optimize airflow. In one embodiment, the apertures are adjustable, and may be closed when air is not flowing through the unit.

Light module 100 also engages air treatment unit 10 at module power socket 40. Particularly, connector 122 mates with module power socket 40, which communicates with an appropriate power source 28 to provide power to UV light source 114 through wires 120. Power source 28, like motor 24, may take many conventional forms. The power transmission, from power source 28 to UV light source 114 is, for the most part, simply generically represented in FIG. 4, it being understood that the provision of power up to the point of connection between module power socket 40 and connector 122, and from there to UV light source 114 will be handled in a conventional manner. Both motor 24 and power source 28 may communicate with individual power switches or with a single power switch, as shown at numeral 25. With this single power switch 25 in base 12, tubing 17 serves as a wire way for the supply of power to UV source 114. In a conventional manner, an electric power cord may communicate with power switch 25 in order to provide power to both fan 22 and UV source 114 upon the operation of switch 25. Likewise, batteries could be employed as the ultimate power source.

When light module 100 is fitted to air treatment unit 10 as disclosed and shown, and unit 10 is activated to start fan 22 and illuminate UV light source 114, UV light source 114 is disposed within air treatment duct 16 and air taken in at intake port 18 passes through baffle 108 and into the interior of air treatment duct 16 is treated with ultraviolet light before being forced out of unit 10 at exhaust port 20.

UV source 114 is preferably a source of UV-C light. Preferably, UV source 114 provides UV energy corresponding to a wavelength of from about 100 to about 280 nanometers (nm). More preferably, UV source 114 provides UV light corresponding to a wave length of about 253.7 nanometers, with a UVGI output of about 2.4 watts, a rated life of about 8,000 hours, and a depreciation curve of only 15 percent at 5,000 hours. One of ordinary skill in the art will appreciate that features such as airflow, dwell time, and bulb intensity may be advantageously modified to promote efficient irradiation of aerosolized microorganisms. Clinical studies have established known standards for inactivating virus, bacterial and mold cells based upon intensity of UV-C radiation and dwell time of the microorganisms within the irradiation device.

In one embodiment, light module 100 and air treatment unit 10 may be optimized to reduce odors through the release of ozone. More particularly, ozone generation can occur as a result of the exposure of oxygen to light at about 185 nanometers. In some applications, where ozone generation is not desired, the glass (i.e. bulb portion) of the UV source is treated to suppress all such energy, resulting in ozone-free operation. However, where ozone generation is desired, a UV source that is treated to allow some output of light corresponding to about 185 nanometers may be selected as UV light source 114. In this embodiment, where light module 100 and air treatment unit 10 are optimized for odor reduction, distinctive markings preferably identify these devices as ozone-generating units. Unique configurations may be employed to prevent the use of a light module that is optimized for ozone generation in an air treatment unit that is intended for ozone-free operation.

Light module 100 may take other forms as necessary to practice the concepts of this invention with air treatment units somewhat dissimilar from air treatment unit 10. Light module 100 not only provides a self-contained light source unit for the replacement of spent UV lights, but also provides safety benefits to a consumer. It will be appreciated from the disclosure above that, when light module 100 selectively engages air treatment duct 16 and connector 122 is selectively connected to module power socket 40, light module 10 cannot be fully removed from its engagement with said air treatment duct. The physical relationship between housing 102, UV light source 114, light source socket 116, wires 120 and connector 122 make it necessary to first disconnect connector 122 from module power socket 40, before light module 100, particularly baffle 108 and UV light source 114, may be removed from engagement with air treatment unit 10. Thus, it is difficult to directly expose oneself to UV light from UV light source 114. The possibility of electrical shock is drastically reduced. Further, said physical relationship ensures proper and optimized orientation of UV light source 114 with respect to fans, reflectors, and other hardware.

In light of the foregoing, it should thus be evident that the process of the present invention, providing an air treatment system for localized and personal use, substantially improves the art. While, in accordance with the patent statutes, only the preferred embodiments of the present invention have been described in detail hereinabove, the present invention is not to be limited thereto or thereby. Rather, the scope of the invention shall include all modifications and variations that fall within the scope of the attached claims.

What is claimed is:

1. An air treatment unit comprising:

a module power socket;

an air treatment duct having an interior defining an air path between a top and bottom of said air treatment duct, said module power socket being located proximate said top; and a light module comprising:

a housing having a baffle, a side wall and a lip, said lip selectively engaged with said top of said air treatment duct, with said sidewall extending downwardly from said lip so that said baffle extends across said air path;

an integral ultraviolet light source and light source socket, said ultraviolet light source being fixed to said light source socket, which is fixed to said baffle, said integral ultraviolet light source and light source socket extending through said baffle, such that said interior of said air treatment duct is exposed to ultraviolet light from said ultraviolet light source when said ultraviolet light source is powered; and a connector located at said lip of said housing, said connector mating with said module power socket, said connector being in power transmissive communication with said light source socket such that said light module cannot be fully removed from its engagement with said air treatment duct without disconnecting the mating of said connector and said module power socket.

2. The air treatment unit of claim 1, wherein said housing of said light module includes a connector flange having an aperture that aligns with said module power socket.

3. The air treatment unit of claim 1, wherein said ultraviolet light source provides UV energy corresponding to a wavelength of from about 100 to about 280 nanometer.

* * * * *